United States Patent [19]

Schaffhausen

[11] 4,396,774

[45] Aug. 2, 1983

[54] USE OF A CATALYST TO INHIBIT FORMATION OF TAR DURING THE "ENE" REACTION OF AN ETHYLENICALLY UNSATURATED ALPHA, BETA DICARBOXYLIC ACID COMPOUND AND AN ETHYLENICALLY UNSATURATED HYDROCARBON

[75] Inventor: John G. Schaffhausen, Aurora, Ill.

[73] Assignee: Standard Oil Company (Indiana), Chicago, Ill.

[21] Appl. No.: 360,372

[22] Filed: Mar. 22, 1982

[51] Int. Cl.$^3$ ............................................. C07D 307/60
[52] U.S. Cl. ..................................... 549/255; 562/595
[58] Field of Search ......................... 549/255; 562/595

[56] References Cited

PUBLICATIONS

Hoffman, Angew, Chem. Internat. Ed., vol. 8, No. 8, (1969).

Snider et al., J.A.C.S. vol. 101, No. 18 (1979).
Batcho et al., Helvetica Chimica Acta, vol. 64(5), 1981 p. 1682–1687.

*Primary Examiner*—Henry R. Jiles
*Assistant Examiner*—Bernard Dentz
*Attorney, Agent, or Firm*—Scott H. Brown; William T. McClain; William H. Magidson

[57] ABSTRACT

A process for the production of a substituted alpha, beta dicarboxylic acid compound substantially free of tar and other resinous reaction byproducts comprising the reaction of an ethylenically unsaturated long chain compound having at least 10 carbon atoms and an ethylenically unsaturated alpha, beta dicarboxylic acid compound at conditions favoring the ENE reaction in the presence of a catalytically effective amount of an alkyl aluminum halide.

10 Claims, No Drawings

USE OF A CATALYST TO INHIBIT FORMATION OF TAR DURING THE "ENE" REACTION OF AN ETHYLENICALLY UNSATURATED ALPHA, BETA DICARBOXYLIC ACID COMPOUND AND AN ETHYLENICALLY UNSATURATED HYDROCARBON

BACKGROUND OF THE INVENTION

1. Field of the Invention

This invention relates to a process for the production of a substantially tar-free "ENE" reaction product of an ethylenically unsaturated alpha, beta dicarboxylic acid compound and an ethylenically unsaturated long chain compound having at least 10 carbon atoms. More particularly this invention relates to a process using an alkyl aluminum halide, such as ethylaluminum dichloride (EtAlCl$_2$), as a catalyst during the "ENE" reaction of an ethylenically unsaturated long chain compound having at least 10 carbon atoms and an ethylenically-unsaturated alpha, beta dicarboxylic acid compound.

2. Setting of the Invention

The "ENE" reaction products can be used for a variety of purposes such as in adhesives, insulating oils, as a raw material in the production of synthetic lubricating oils, preservatives, polyesters, additives in lubricants and fuels, etc. A very important use of these products is as a raw material for the manufacture of additives to improve the characteristics of fuels and lubricants. Most commonly, the reaction product of a substituted dicarboxylic acid compound, and an amine compound, such as a polyamine, can be used in gasolines and lubricants. These additives are often useful in fuels such as gasolines to inhibit rust, carburetor deposits, carburetor icing, etc., and as dispersants in motor oils to prevent the formation of harmful deposits on engine surfaces caused by oxidation products of lubricants and fuels, wear products, ingested dirt, etc.

The "ENE" reaction between an ethylenically unsaturated long chain compound having at least 10 carbon atoms and an alpha, beta unsaturated dicarboxylic acid compound involves the addition of the unsaturated long chain compound having at least 10 carbon atoms to one of the vinyl carbons of the unsaturated dicarboxylic acid compound. An example of the reaction is the addition of polyisobutylene to maleic anhydride:

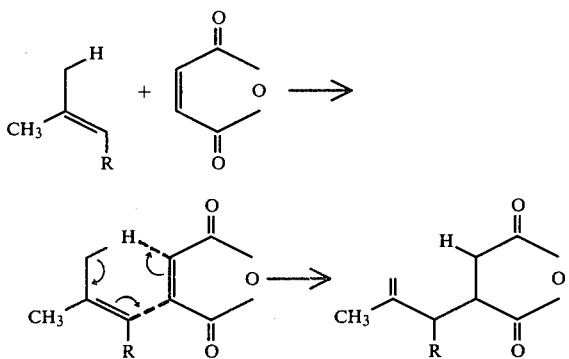

The uncatalyzed "ENE" reaction between an ethylenically unsaturated long chain compound having at least 10 carbon atoms and an ethylenically unsaturated alpha, beta dicarboxylic acid compound has a major drawback. The unsaturated dicarboxylic acid compound suffers decomposition at elevated temperatures causing the formation of tar and other resinous byproducts. Thermal decomposition of ethylenically unsaturated alpha, beta dicarboxylic acid compounds at temperatures in excess of 100° C. has been known and reported, for example, in U.S. Pat. No. 3,476,774. Such thermal decomposition can be accompanied by the evolution of water vapor and oxides of carbon. Under some observed conditions, the thermal decomposition can be explosive. In the absence of explosive decomposition, the thermal decomposition of the reactants and reaction products form carbon containing residues which are manifest in granular and tarry forms. Since the granular residue tends to remain suspended in the reaction product and cannot be removed easily therefrom, the desired product has a poor color rating and is often commercially unacceptable. The resinous tar-like residue tends to coat the internal surface of the reaction vessel, thereby necessitating the periodic shutdown and cleaning of the tarry material from the reactors. Obviously, the destruction of the ethylenically unsaturated alpha, beta dicarboxylic acid compound by thermal decomposition is also economically undesirable.

A variety of tar and resinous byproduct inhibitors for the "ENE" reaction have been proposed by the prior art. In general there are at least four types of inhibitors: (1) substituted benzene sulfonic acids, (2) halogenated compounds such as halogenated polymers or dibromohydantoin, (3) phenothiazine and quinone-type compounds and (4) boron compounds. These inhibitors have met with various degrees of success in reducing the formation of tars.

The tar is substantially a thermal decomposition product of the unsaturated dicarboxylic acid compound and the "ENE" reaction which is normally run at temperatures of between 100° C. to 300° C., preferably from about 200° to 250° C. It appears that it is the high temperature reaction environment which causes the formation of the tar and other resinous material. Therefor, there exists a need for a process which can reduce the temperature requirements of the "ENE" reaction of ethylenically unsaturated alpha, beta dicarboxylic acid compounds and an ethylenically unsaturated long chain compound having at least 10 carbon atoms, thereby reducing the energy requirements for the reaction and further reducing the formation of tar and other resinous byproducts.

The use of an alkyl aluminum halide as a Lewis acid catalyst to reduce the temperature requirements in the reaction of methyl propiolate with unactivated alkenes is disclosed in Snider, J. et al., *Lewis Acid Catalyzed Reactions of Methyl Priopiolate with Unactivated Alkenes,* Journal American Chemical Society 101, 5283 (1979). However, nowhere is it disclosed within Snider to use the alkyl aluminum halide to reduce the temperature requirements of and prevent the formation of tar in the reaction of ethylenically unsaturated alpha, beta dicarboxylic acid compound and an ethylenically unsaturated long chain compound having at least 10 carbon atoms. The use of other catalysts in the "ENE" reaction is disclosed in Hoffmann, H., *The Ene Reaction,* Agnew. Chem. Intl. Ed. Vol. 8, p. 556 (1969). However nowhere is it disclosed in Hoffmann to use an alkyl aluminum halide as a catalyst in the reaction of ethylenically unsaturated alpha, beta dicarboxylic acid compound and an ethylenically unsaturated long chain compound having at least 10 carbon atoms.

DESCRIPTION OF THE PREFERRED EMBODIMENTS

It has been found that the "ENE" reaction of an ethylenically unsaturated long chain compound having at least 10 carbon atoms and an ethylenically unsaturated alpha, beta dicarboxylic acid compound can be enhanced in the presence of an effective amount of an alkyl aluminum halide. The alkyl aluminum halide acts as a catalyst to reduce the reaction temperature requirements of the "ENE" reaction thereby eliminating or substantially reducing the formation of tar and other resinous byproducts. The process of the invention is performed by reacting an ethylenically unsaturated long chain compound having at least 10 carbon atoms with an unsaturated alpha, beta dicarboxylic acid compound in the presence of an effective amount of an alkyl aluminum halide, such as ethylaluminum dichloride, at temperatures as low as about 0° C., and preferably from 0° C. to about 60° C.

Throughout this discussion of "ethylenically unsaturated hydrocarbon" means an unsaturated long chain compound having at least 10 carbon atoms. Such compounds are further discussed herein below. The alkyl aluminum halides effective for use in this invention include compounds having the general formula of:

$$R_nAlX_{3-n}$$

wherein: each R is independently any suitable organic radical including alkyl groups of 1–8 carbon atoms, such as methyl-, ethyl-, propyl-(n or iso), butyl-(n or secondary, tertiary), n-octyl, 2-ethyl hexyl etc.; X is halogen (preferably chloro or bromo); and $0 \leq n \leq 3$.

Other materials which could be substituted for Al include In, Ga, or Tl. Other compounds which could be used include $SiCl_4$, $GeCl_4$, $SbCl_3$, $SbCl_5$, $VCl_3$, $SnCl_4$, or a compound having the general formula of:

$$TiX_n(OR)_{4-n}$$

wherein: R is any suitable organic; X is a halogen; and $0 \leq n \leq 4$.

The use of the alkyl aluminum halides listed above give excellent yields of products uncontaminated with a halogen. Further, the products produced have a golden, honey color which is far lighter in color than the majority of the products produced by the prior art processes. The light color gives a visual indication of the almost total elimination of tars or resinous byproducts in the product. It is believed that this dramatic improvement is due to the ability of the alkyl aluminum halide to act as a proton scavenger as well as a Lewis acid. The "ENE" reaction using ethylaluminum dichloride ($EtAlCl_2$) as a catalyst is illustrated below, specifically the schematic illustration shows the reaction of polybutene with maleic anhydride, in methylene chloride as a solvent, to produce hydrocarbyl succinic anhydride.

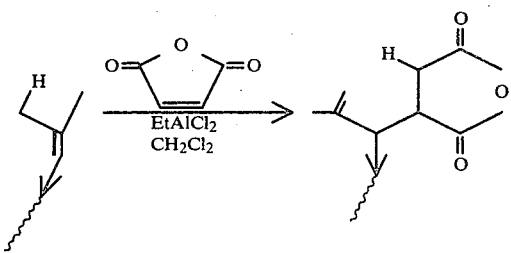

Ethylenically unsaturated hydrocarbons useful in the "ENE" reaction of this invention are substantially hydrocarbon compounds containing from about 10 to about 430 carbon atoms and containing from about 1 to about 4 olefinic bonds. The olefinic compounds can contain other functional groups such as carbonyls, carboxyl groups, halide groups, alkyl and aryl substituents, organometallic groups, sulfur containing groups, etc. The important characteristic is that at least one ethylenically unsaturated group with at least one allylic hydrogen atom is present for the "ENE" reaction. In the absence of the allylic hydrogen the olefin must be capable of isomerizing under reaction conditions to an olefin containing an allylic hydrogen substituent. Substituents which increase the electron density of the double bond also facilitate the reaction. Suitable ethylenically unsaturated hydrocarbons include decene, isodecene, dodecene, tertiary dodecene, 2-ethyldecene, eicosene, pentacontene, etc. These compounds can be derived directly from refinery streams, or can be produced by the oligomerization of olefins such as ethylene, propene, or butene. Other ethylenically unsaturated hydrocarbons that can be used are polymers produced by the polymerization of common olefinic monomers such as ethene, propene, 1-butene, 2-butene, and isobutylene. These polymers commonly have a molecular weight from about 140 to about 6,000 as produced by commercial well-known polymerization techniques.

Preferably for reasons of availability, low cost, and high reactivity, viscous polyalkene polymers or olefinic monomers are preferred. These polymers can contain up to about 430 carbon atoms and are prepared from alkene monomers such as ethene, propene, 1-butene, cis- and trans-2-butene, and isobutylene. The viscous polyalkene polymers are commonly produced by the polymerization of the alkene stream under pressure in contact with an aluminum chloride catalyst. The preferred polyalkenes for reasons of high activity and low cost are polypropene, polyisobutylene and polybutene having a molecular weight between 140 and about 6,000, preferably for ease of reaction and high activity, a molecular weight of about 200 to about 3,000 is used.

Ethylenically unsaturated alpha, beta dicarboxylic acid compounds useful in the "ENE" reaction include maleic anhydride, maleic acid, fumaric acid, citraconic anhydride, citraconic acid, itaconic anhydride, itaconic acid, ethyl maleic anhydride, ethyl maleic acid, halo (e.g., chloro) maleic anhydride, etc. Preferably, for ease of reaction and low cost, maleic acid or maleic anhydride can be used.

In somewhat greater detail, the "ENE" reaction between the ethylenically unsaturated hydrocarbon and the ethylenically unsaturated alpha, beta dicarboxylic acid compound is carried out in standard commercial well-known procedures. The art recognizes both batchwise reaction or continuous reaction in stirred tanks, pressurized reactors, continuous reaction zones, or other equivalent reaction vessels to provide intimate contact between the reactants.

For batchwise operation the reactants are charged to the closed reaction vessel with or without an inert (oxygen-free) atmosphere, such as nitrogen, at ambient or elevated pressure. The reactants can be added to the vessel at ambient temperature. However, the ethylenically unsaturated hydrocarbon can be used at an elevated temperature to reduce the time for reaction and to reduce viscosity. The ethylenically unsaturated alpha, beta dicarboxylic acid compound can be charged in solid form or dispersed in a portion of the unsaturated hydrocarbon or can be heated and added to the reactant mixture as a melt. During the reaction the mixture is stirred while the reaction temperature is controlled. Convenient conduct of the reaction can be maintained by charging to the reaction vessel a melt of the ethylenically unsaturated alpha, beta dicarboxylic acid compound and preheated ethylenically unsaturated hydrocarbon so that the combined reactants provide sufficient heat to drive the reaction. At the end of the reaction, excess dicarboxylic acid compound can be removed by distillation. The product which can contain minor amounts of unsaturated hydrocarbon can be filtered and used. Reaction time for batchwise operation can be 2 to 24 hours and greater.

In continuous operation, ambient or heated streams of dicarboxylic acid compound and unsaturated hydrocarbon can be charged to one end of a horizontal or vertical reaction zone. The reactants can be intimately contacted within the zone for a sufficient time at a sufficient temperature and pressure. The product can be withdrawn from the zone to appropriate strippers and filters. In order to minimize formation of solid or tarry or resinous degradation products, the reaction can be carried out with a continuous dicarboxylic acid compound reflux. The reflux rate can be in slight excess of the reaction requirements for the dicarboxylic acid compound. In this way the reaction solution is kept saturated with dicarboxylic acid compound throughout the reaction. Any dicarboxylic acid compound in excess over that required to saturate the reaction zone continuously distills from the reaction zone overhead avoiding the appearance of separate dicarboxylic acid compound phase in the reactor and the consequent contamination of the reaction product. The reduction in the concentration of the dicarboxylic acid compound also reduces the products of degradation. The unsaturated hydrocarbon feed can also be controlled so that the rate of reflux and the feed rate of the unsaturated hydrocarbon are balanced to match the stoichiometric ratio of reactants. In continuous operation a shorter residence time is possible, for example 1 to 8 hours.

The alkyl aluminum halide can be added to the "ENE" reaction in the batch or continuous process in any convenient manner. For example, the alkyl aluminum halides can be suspended or dissolved in either reactant stream. Alternately, the alkyl aluminum halide can be directly added to the reactor or can be dissolved in an inert solvent, such as pentane, heptane, gasoline, kerosene, lubricating oil fractions, benzene, toluene, etc., prior to addition.

The amount of alkyl aluminum halide used in the "ENE" reaction can be, on a mole basis, from about 20 percent to about 100 percent per mole of the ethylenically unsaturated hydrocarbon. Commonly the reaction can be run at molar ratios of about 0.5 to about 10 moles of ethylenically unsaturated alpha, beta dicarboxylic acid compound per mole of ethylenically unsaturated hydrocarbon. Preferably, the reaction is run with a slight excess of ethylenically unsaturated hydrocarbon. For example, from about 1 to about 1.5 moles of unsaturated hydrocarbon is reacted with about 1 mole of unsaturated dicarboxylic acid compound. The prior art reaction can be run at ambient to high pressure at temperatures from about 100° C. to about 300° C. However, with the use of an alkyl aluminum halide catalyst, the reaction can take place at temperatures from between 0° C. to about 150° C. or to about 300° C., if desired. Preferably, the reaction can take place at room temperature (19°–28° C.). The upper temperature limit may be set by the boiling point of the solvent used in the reaction, such as 60° C. for hexane.

The following examples are provided for illustrative purposes only and are in no way to limit the scope or coverage of this invention.

EXAMPLE I: Inertness of Polybutene to EtAlCl$_2$

To a dry 500 ml, one-neck flask under injection of nitrogen was added at room temperature (25° C.) sequentially 99 parts (75 ml) of methylene chloride, 7.7 parts (21.4 ml) of EtAlCl$_2$ in solution (approximately 3 molar EtAlCl$_2$ in hexane, 64.2 mmoles). The flask and contents were cooled to 0° C. Twenty seven parts of (27.0 g) of polybutene (m.w. 420, 64.2 mmoles) in 66 parts (50 ml) of methylene chloride was added and thereafter the flask and contents were allowed to reach room temperature (25° C.). After 25 hours the catalyst was quenched by the controlled addition of 8 parts (10 ml) of ethanol. Then 10 percent hydrochloric acid was added to the flask. The resulting layers were separated and the organic layer was diluted with hexane, washed with a small amount of additional hydrochloric acid, dried over anhydrous magnesium sulfate, filtered and evaporated to 200° C. under a nitrogen stream. The viscosity of the isolated polymer was 102 cs (100° F.), whereas the starting material had a viscosity of 106–112 cs.

EXAMPLE II: Preparation of Succinic Anhydride

To a dry 500 ml, one-neck flask under injection of nitrogen was added at room temperature sequentially 99 parts (75 ml) of methylene chloride, 7.7 parts (21.4 ml) of EtAlCl$_2$ in solution (approximately 3 molar EtAlCl$_2$ in hexane, 64.2 m moles). The flask and contents were cooled to 0° C. Twenty seven parts (27.0 g) of polybutene (Amoco L-50, obtained from Amoco Chemicals Corporation) with a molecular weight of 420, 64.2 mmoles, dissolved in 66 parts (50 ml) of methylene chloride was added. Thereafter, 5.7 parts (5.66 g, 57.8 mmoles) of maleic anhydride in 66 parts (50 ml) of methylene chloride was added. Thereafter the flask and contents were allowed to reach room temperature (25° C.). After 25 hours the catalyst was quenched by the controlled addition of 8 parts (10 ml) of ethanol. Then 10% hydrochloric acid was added to the flask. The resulting layers were separated and the organic layer was diluted with hexane, washed with a small amount of additional hydrochloric acid, dried over anhydrous magnesium sulfate, filtered and evaporated at 200° C. under a nitrogen stream. Twenty three and one-half parts of a bright, clear residue was produced with IR absorptions at 1780 and 1710 cm$^{-1}$. This residue was dissolved in 40 parts (50 ml) of xylene, 19.8 parts of diethylenetriamine (DETA) was added and the solution was refluxed for two hours. After evaporation to 200° C. under nitrogen, a viscous product was obtained which had the expected imide IR absorption. It was determined that the produced polymer was 76 percent functionalized by chromotography on silica with hexane.

EXAMPLE III: Preparation of Succinic Anhydride

The procedures in accordance with Example II were followed using 103 parts (102.7 g) of polybutene (Amoco H-1500, obtained from Amoco Chemicals), with a molecular weight of approximately 1600, 64 mmoles, in 200 parts (150 ml) of methylene chloride in place of the L-50 polybutene solution. After 24 hours, the solution was cooled to 0° C. and 150 parts (150 ml) of a 20 percent solution of $AlCl_3 \cdot 6H_2O$ in water was added. The produced organic layer was separated and treated as in Example II. A viscous, clear product was obtained which had IR absorptions at 1860, 1760 (strongest) and 1700 cm$^{-1}$. Thereafter, 34 parts (34 g) of the product was dissolved in 60 parts (75 ml) of xylene and reacted with 4.9 parts (4.9 g) of DETA. The resulting product had a small IR absorption at 1760 and a large absorption at 1700 cm$^{-1}$. It was determined that the product polymer was 31 percent functionalized by chromatography on silica with hexane.

The results from Example II and III utilized one equivalent of $EtAlCl_2$ for the hydrocarbyl succinic anhydride to give activities of 76 percent and 31 percent, respectively. Further tests were conducted to define the amount of alkyl aluminum halide required in the "ENE" reaction. The results are summarized in Table 1. It is apparent that reductions in catalyst requirements up to 80 percent of the theoretical amount (1 eq.) do not seriously lower product activity. Further optimization of reaction conditions could enhance the product activity.

Equivalents are calculated by assuming one double bond per polybutene molecule with molecular weights of 420 for Example II and 1600 for Example III. For example, 27 g of polybutene used in Example II represents 0.064 reactive units; 0.064 reactive units of catalyst solution is 1.0 equivalent and 0.032 reactive units of catalyst solution is 0.5 equivalent and so on.

TABLE 1

| Polybutene | Equivalents of EtAlCl$_2$ | Parts Polymer | Parts EtAlCl$_2$ | Activity of Produced Succinic Anhydride |
|---|---|---|---|---|
| L-50 | 1.0 | 27 | 7.7 | 76% |
| L-50 | 0.4 | 27 | 3.1 | 44% |
| L-50 | 0.2 | 27 | 1.5 | 49% |
| H-1500 | 1.0 | 103 | 7.7 | 31% |
| H-1500 | 0.6 | 103 | 4.6 | 33% |
| H-1500 | 0.4 | 103 | 3.1 | 37% |
| H-1500 | 0.2 | 103 | 1.5 | 26% |

The hydrocarbyl succinic anhydrides formed by this invention can serve as succimide precusors for a variety of end uses, such as crude oil antifoulants, carburetor detergents, two stroke engine additives and general purpose dispersants. The mildness (the low temperatures used and the nondegrading nature or nondestructive nature of the alkyl aluminum halides as catalyst) of the reaction should be a distinct processing advantage over the current thermal processes. The prevention of tar formation in the process of this invention (a) produces a very high quality, excellently colored product, (b) does not require tar supressant additives and (c) does not require costly tar cleanup in the reaction vessel. Another advantage of this catalyst is that the process may be used in the manufacture of higher molecular weight compounds for Viscosity Index Improvers and Cold Flow Improvers, where polymer thermal degradation is a severe limitation. Further, the process of this invention can be carried out at room temperature which greatly decreases the energy required to produce these products of an "ENE" reaction.

Whereas the present invention has been described in relation to the examples and table included herein, other and further modifications of the invention, apart from those suggested herein, may be made within the scope and spirit of this invention.

I claim:

1. A process for the production of a substituted alpha, beta dicarboxylic acid compound substantially free of tar and resinous reaction byproducts which comprises the reaction of an ethylenically unsaturated alpha, beta dicarboxylic acid compound with an ethylenically unsaturated long chain compound having at least 10 carbon atoms at conditions favoring the "ENE" reaction in the presence of a catalytically effective amount of an alkyl aluminum halide.

2. The process of claim 1 wherein the alkyl aluminum halide is present in the reaction mixture at a concentration of about 1 to 100,000 parts by weight per million parts by weight of ethylenically unsaturated long chain compound having at least 10 carbon atoms.

3. The process of claim 2 wherein the alkyl aluminum halide is an alkyl aluminum dihalide.

4. The process of claim 3 wherein the ethylenically unsaturated long chain compound having at least 10 carbon atoms comprises a substantially linear hydrocarbon having a molecular weight of from 140 to 6,000.

5. The process of claim 4 wherein the ethylenically unsaturated long chain compound having at least 10 carbon atoms comprises polyisobutylene or polypropene.

6. The process of claim 1 wherein the ethylenically unsaturated aliphatic dicarboxylic acid compound comprises maleic acid or maleic anhydride.

7. The process for the production of substituted succinic acid compound substantially free of tar and resinous reaction byproducts which comprises the reaction at conditions favoring the "ENE" reaction of an ethylenically unsaturated long chain compound having at least 10 carbon atoms and maleic anhydride in the presence of a catalytically effective amount of ethylaluminum dichloride.

8. The process of claim 7 wherein the ethylenically unsaturated long chain compound having at least 10 carbon atoms is a substantially linear hydrocarbon having a molecular weight from about 140 to 6,000.

9. The process of claim 6 wherein the ethylenically unsaturated long chain compound comprises polyisobutylene and polypropene.

10. The process of claim 8 wherein the ethylaluminum dichloride is present at a concentration of about 1 to 100,000 parts by weight per million parts by weight of ethylenically unsaturated long chain compound having at least 10 carbon atoms.

* * * * *